(12) United States Patent
Demarco et al.

(10) Patent No.: US 9,157,803 B2
(45) Date of Patent: Oct. 13, 2015

(54) SPECTROMETER AND METHOD OF SPECTROSCOPY

(71) Applicant: THERMO FISHER SCIENTIFIC (ECUBLENS) SARL, Ecublens (CH)

(72) Inventors: Fabio Demarco, Lausanne (CH); Jean-Luc Dorier, Bussigny-Lausanne (CH); Edmund Halasz, Ecublens (CH)

(73) Assignee: Thermo Fisher Scientific (Ecublens) SARL, Ecublens (CH)

( * ) Notice: Subject to any disclaimer, the term of this patent is extended or adjusted under 35 U.S.C. 154(b) by 0 days.

(21) Appl. No.: 14/361,840

(22) PCT Filed: Dec. 11, 2012

(86) PCT No.: PCT/EP2012/075064
§ 371 (c)(1),
(2) Date: May 30, 2014

(87) PCT Pub. No.: WO2013/087617
PCT Pub. Date: Jun. 20, 2013

(65) Prior Publication Data
US 2014/0368818 A1    Dec. 18, 2014

(30) Foreign Application Priority Data

Dec. 14, 2011 (GB) .................................. 1121427.7

(51) Int. Cl.
*G01J 3/28* (2006.01)
*G01J 3/443* (2006.01)
*G01J 3/02* (2006.01)
*G01J 3/18* (2006.01)
*G01N 21/67* (2006.01)

(52) U.S. Cl.
CPC ................ *G01J 3/443* (2013.01); *G01J 3/021* (2013.01); *G01J 3/024* (2013.01); *G01J 3/0208* (2013.01); *G01J 3/0229* (2013.01); *G01J 3/0294* (2013.01);*G01J 3/18* (2013.01); *G01J 3/2803* (2013.01); *G01N 21/67* (2013.01)

(58) Field of Classification Search
CPC ....... G01N 21/67; G01N 21/69; G01N 33/20; G01J 3/02; G01J 3/18; G01J 3/28; G01J 3/2803; G01J 3/2823; G01J 3/443
USPC .................................................. 356/300–334
See application file for complete search history.

(56) References Cited

U.S. PATENT DOCUMENTS

2001/0028462 A1*  10/2001  Ichihara et al. ............... 356/512
2008/0084562 A1*   4/2008  Canioni et al. ............... 356/318
2008/0309936 A1   12/2008  Krapu

FOREIGN PATENT DOCUMENTS

| EP | 1099942 A1 | 5/2001 |
| FR | 2956204 A1 | 8/2011 |
| JP | 2006300671 A2 | 11/2006 |

*Primary Examiner* — Abdullahi Nur
(74) *Attorney, Agent, or Firm* — William R. McCarthy, III

(57) ABSTRACT

A spark optical emission spectrometer comprising: a spark source for causing spark induced emission of light from a sample; a single entrance slit; a toroidal mirror for directing the light through the single entrance slit; a plurality of diffraction gratings for diffracting light that has been directed through the entrance slit by the mirror, whereby the plurality of diffraction gratings are simultaneously illuminated; and at least one array detector for detecting the diffracted light from the plurality of diffraction gratings, wherein the minor is for directing the light through the entrance slit such that light from different regions in the spark source is spatially separated in an image of the light at the gratings whereby a first diffraction grating is preferentially illuminated with light from a first region of the spark source and simultaneously a second diffraction grating is preferentially illuminated with light from a second region of the spark source.

18 Claims, 5 Drawing Sheets

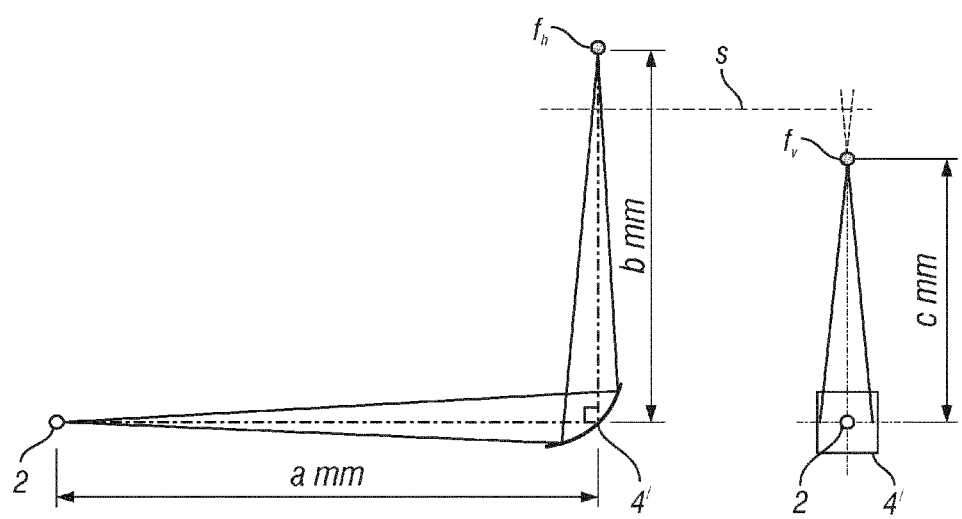
FIG. 3
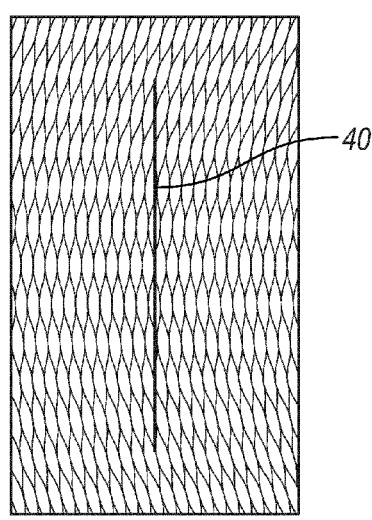
FIG. 4
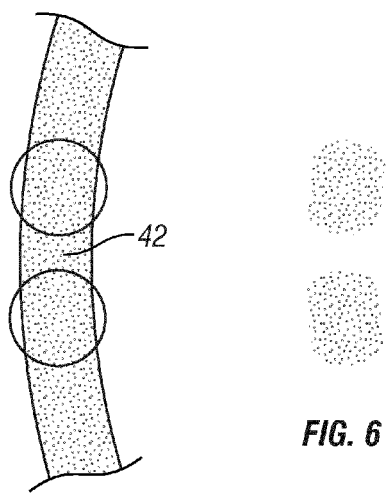
FIG. 5
FIG. 6

SPECTROMETER AND METHOD OF SPECTROSCOPY

CROSS-REFERENCE TO RELATED APPLICATIONS

This application is the U.S. National Stage Application, under 35 USC 371, of International Application No. PCT/EP2012/075064 having an international filing date of Dec. 11, 2012 and designating the United States, which claims priority to GB 1121427.7, filed Dec. 14, 2011, said applications incorporated by reference herein in their entireties.

FIELD OF THE INVENTION

The present invention relates to a spectrometer, particularly but not exclusively, a spectrometer for optical emission spectroscopy.

BACKGROUND OF THE INVENTION

Optical emission spectroscopy (OES) is a technique for the elemental analysis of samples, known also as Atomic Emission Spectroscopy (AES). OES uses the intensity of light at a particular wavelength emitted from a sample subjected to, for example, a flame, plasma, arc, or spark to determine the quantity of an element in a sample. Light is emitted by the excited atoms and ions of the elements of the sample as transitions occur from an excited state to a lower energy state. Each element emits light of discrete wavelengths characteristic of its electronic structure, which are also termed spectral lines. By separating and detecting the spectral lines, OES can provide a qualitative and quantitative determination of the elemental composition of the sample. The spectrometer of the present invention is particularly suitable for so-called spark OES, which is useful, for example, in the analysis of solid metallic samples. In spark OES, an electrical discharge, such as a condensed arc or spark for example, is used to rapidly vaporise a solid sample and excite elements in the vapourised sample. A spark OES spectrometer includes a spark stand or chamber for ablating the sample material and exciting the elements in the sample to emit light, an optical system for dispersing the emitted light into discrete wavelengths and a detection system for detecting the intensity of the dispersed light. Furthermore, the spectrometer typically comprises a data processing and storage system for processing and storing signals from the detection system, e.g. representing the light intensity. To build up sufficient data for determination of the composition, a succession of sparks is typically employed and the resulting data generated from the sparks is accumulated for processing.

A known type of spectrometer optics for OES is the flat field spectrometer in which the dispersed light is imaged substantially linearly at one or more detectors over the spectral range of interest. This enables the use of a flat surface detector, typically a charge coupled device (CCD). A flat field spectrometer is particularly suitable for use with a linear CCD detector. Double or triple flat field spectrometers may be constructed in which two or three separate gratings may be used, each of which receive light from the sample through their own respective entrance slit. The separate gratings each form a separate spectrum in a different spectral range on its own respective detector. Such double or triple flat field spectrometers are thus more bulky than single flat field spectrometers since they respectively require two or three entrance slits, two or three gratings and two or three detectors. In such systems, each entrance slit requires its own viewing angle of the sample plasma, which must be accommodated.

A compact double flat field spectrometer is disclosed in WO 2011/098726. In this document, instead of using one entrance slit per grating and a separate detector, a flat field spectrometer is described which comprises only one entrance slit but two diffraction gratings and one detector having a plurality of lines of photodetectors. The single detector is thus an array detector. Each grating diffracts a portion of the light received through the entrance slit and each grating forms a spectrum on a separate line of the array detector. In this way, a double flat field spectrometer is constructed that is very compact and low cost whilst covering a relatively broad spectral range. The present invention is particularly, although not exclusively, applicable to a compact double flat field spectrometer as disclosed in WO 2011/098726. In fact, both the flat field spectrometer disclosed in WO 2011/098726 and the present invention can be used with more than two gratings. For example, a compact flat field spectrometer is disclosed in WO 2011/098726 having four diffraction gratings that each receive light through the single entrance slit.

A problem with OES, which is not addressed by the spectrometer disclosed in WO 2011/098726, is that of spectral interference. This is where a spectral line of analytical interest is interfered with by another spectral line at similar or the same wavelength as the line of analytical interest. In this way, the partial or complete overlap of the spectral lines means that it is difficult to extract information from the line of analytical interest.

A further challenge in an optical arrangement for spark OES is to pass towards the gratings and detector as much as possible of the light that is analytically needed and/or to reduce the high excitation energy background, which is emitted near the sample surface. It is another challenge to illuminate constantly the grating in order to obtain a constant resolving power.

Against this background, the present invention has been made.

SUMMARY OF THE INVENTION

According to the present invention there is provided a spectrometer comprising: a single entrance slit; a toroidal mirror for directing light to be analysed through the single entrance slit; a plurality of diffraction gratings for diffracting light that has been directed through the entrance slit by the mirror, whereby the plurality of diffraction gratings are simultaneously illuminated by the light; and at least one array detector for detecting the diffracted light from the plurality of diffraction gratings.

According to another aspect of the present invention there is provided a method of spectroscopy comprising: directing light to be analysed through an entrance slit using a toroidal mirror; simultaneously illuminating a plurality of diffraction gratings with the light directed through the entrance slit, whereby each diffraction grating diffracts a portion of the light; and detecting the diffracted light.

According to yet another aspect of the present invention there is provided a spark optical emission spectrometer comprising: a spark source for causing spark induced emission of light to be analysed from a sample; a single entrance slit; a toroidal mirror for directing the light through the single entrance slit; a plurality of diffraction gratings for diffracting light that has been directed through the entrance slit by the mirror, whereby the plurality of diffraction gratings are simultaneously illuminated; and at least one array detector for detecting the diffracted light from the plurality of diffraction gratings, wherein the mirror is for directing the light through the entrance slit such that light from different regions in the spark source is spatially separated in an image of the light at the gratings whereby a first diffraction grating is preferentially illuminated with light from a first region of the spark source and simultaneously a second diffraction grating is preferentially illuminated with light from a second region of the spark source.

According to yet another aspect of the present invention there is provided a method of spark optical emission spectroscopy comprising: directing spark induced emission of light to be analysed from a spark source through an entrance slit using a toroidal mirror; simultaneously illuminating a plurality of diffraction gratings with the light directed through the entrance slit, whereby each diffraction grating diffracts a portion of the light; and detecting the diffracted light from the plurality of diffraction gratings using at least one array detector; wherein the mirror directs the light through the entrance slit such that light from different regions in the spark source is spatially separated in an image of the light at the gratings whereby a first diffraction grating is preferentially illuminated with light from a first region of the spark source and simultaneously a second diffraction grating is preferentially illuminated with light from a second region of the spark source.

DETAILED DESCRIPTION OF THE INVENTION

The invention is preferably designed to be a flat field based optics spectrometer. Thus, the spectrometer optics comprises flat field mounting of the entrance slit, the gratings and the at least one detector. More preferably, the spectrometer is an optical emission spectrometer and the method is optical emission spectroscopy. The present invention has a particularly preferred application as a spark optical emission spectrometer.

Advantageously, the use of a toroidal mirror has been found to enable the efficient illumination of both gratings, especially simultaneously. Different regions in the light source can be spatially separated in the image formed at the gratings, which has been found to be analytically useful. In prior designs, in order to preferentially collect the light from a given region of the plasma, different solid angles of observation were associated with separate optics. In the present invention, using a single solid angle of observation of the source, for example, a first diffraction grating may be preferentially illuminated with light from a first region of the light source compared to a second grating and the second grating may be preferentially illuminated with light from a second region of the light source compared to the first grating. In the application as a spark optical emission spectrometer, this realization enables light from different regions or points of the spark light source to be spatially separated to a degree at the gratings. For example, a first diffraction grating may be preferentially illuminated with light from a first region of the spark light source compared to a second grating and the second grating may be preferentially illuminated with light from a second region of the spark light source compared to the first grating. This leads to a further advantage that certain spectral interferences can be resolved, i.e. reduced, since there is not such a strong mixture of spectral information gathered by each grating. For example, two spectral lines from two different elements may occur at similar or the same wavelength thereby causing spectral interference in the usual case. However, if the excitation events which lead to the emission of these spectral lines occur in different regions of the spark light source (e.g. due to a temperature distribution in the spark plasma), then the present invention is more able to reduce the degree of spectral interference. The optical arrangement of the present invention with the toroidal mirror therefore acts as a kind of geometrical filter on the light from the spark source.

Efficiently, only a single toroidal mirror is used in the present invention to illuminate two or more gratings instead of two or more mirrors or lenses or fibre optics being required. Preferably, the toroidal mirror is placed before the entrance slit for collecting light to be analysed directly from the spark source without any intervening optics. In other words, the toroidal mirror is preferably placed before the entrance slit without any mirrors or lenses between the source and the toroidal mirror and preferably also without any mirrors or lenses between the toroidal mirror and the entrance slit. In preferred embodiments, the toroidal mirror is the sole (i.e. the only) mirror in the spectrometer. Moreover, lenses preferably are not used in the spectrometer, i.e. lenses preferably are not used in the optical path of the light between the source and the detector. The sole toroidal mirror allows imaging of the spark source at the plurality of gratings and resolution of certain spectral interferences.

Preferably, only a single entrance slit is provided. The present invention beneficially enables a plurality of diffraction gratings to be achromatically illuminated through a single entrance slit. Hitherto, OES spectrometers have typically used lenses or spherical mirrors to focus light emitted from a sample through the entrance slit(s) to the grating(s). The present invention, in contrast, employs a single toroidal mirror to reflect light to be analysed towards a single entrance slit. The toroidal mirror, being aspherical, has been found to be more efficient to illuminate two or more diffraction gratings simultaneously through a single slit, i.e. with less light wastage. The generally elliptical shape of the light image produced by the toroidal mirror is better matched, for example, to the geometrical arrangement of two mounted diffraction gratings, especially two vertically mounted gratings. The vertical position of the gratings enables the observation of specific spark plasma zones (in a spark source) related to the thermal distribution in the spark plasma.

The diffraction gratings are for receiving and diffracting light that has been directed through the entrance slit by the mirror. The diffraction gratings are preferably designed for flat field mounting, i.e. to provide a flat field image at the at least one array detector. The plurality of diffraction gratings is preferably two, three or four gratings, most preferably two gratings. Thus, in the most preferred embodiment having two gratings, the spectrometer comprises a double spectrograph, especially a double flat field spectrograph.

The gratings are preferably holographic gratings. The gratings are preferably aberration corrected flat field and imaging gratings. The gratings are preferably designed for high efficiency in the first order of diffraction.

The gratings are preferably mounted separately, i.e. independently. The gratings are preferably mounted adjacent to each other and more preferably are mounted close together. The gratings are preferably mounted at substantially the same distance as each other from the entrance slit. The gratings are similarly preferably mounted at substantially the same distance as each other from the at least one detector. Each diffraction grating diffracts a different portion of the light received through the entrance slit.

In the embodiments having two diffraction gratings, the gratings are preferably mounted vertically with respect to each other. Generally, the centres of the light source, the toroidal mirror and the entrance slit lie in a plane, referred to as the horizontal plane. In this context, vertical means perpendicular to this horizontal plane. Vertical is preferably also the direction of elongation of the entrance slit. Vertical in this context also preferably is the direction of the axis of the toroidal mirror that has the smaller radius of curvature (toroidal mirrors have two orthogonal axes with smaller and larger radiuses of curvature respectively). In the embodiments where the spectrometer is for spark OES, vertically mounted preferably also means mounted substantially in the direction of a line between the electrode and the sample in the spark chamber of a spark optical emission spectrometer.

Preferably, each grating forms a spectrum on the at least one detector in a different spectral range to the other grating(s). Thereby, the plurality of spectra in different spectral ranges can be combined to provide a spectrum covering a broad spectral range. Thus, the present invention allows continuous coverage of a given spectral range in multiple parts with given resolution. Such grating systems are described in WO 2011/098726.

The spectrometer preferably covers at least the range from 147 to 418 nm, i.e. the plurality of gratings together allows continuous coverage of this spectral range. For example, one grating may provide diffracted light for detection over a spectral range 147-238 nm and another grating may provide diffracted light for detection over a spectral range 230-418 nm. Thus, each grating is designed for specific wavelength coverage. Accordingly, the at least one array detector is designed to detect light continuously across the wider spectral range. These particular ranges are especially applicable in the case where the spectrometer is a spark optical emission spectrometer.

The at least one detector for detecting the diffracted light is preferably an array of photodetectors. Preferably, each grating forms a spectrum on a separate sub-array of photodetectors within the array. More preferably, the array of photodetectors comprises a plurality of separate lines of photodetectors (i.e. each line thereby constituting a sub-array of photodetectors). Even more preferably, in such embodiments, as each diffraction grating diffracts a portion of the light received through the entrance slit, each grating forms a spectrum on a separate line of photodetectors. Preferably, a suitable separation distance is provided between such sub-arrays or lines of photodetectors to avoid a spectrum from one grating falling on an array or line of photodetectors intended for detecting the spectrum from another grating. The separation distance may comprise a space or one or more intermediate lines of photodetectors not used for detection. Preferably, in the preferred embodiment of having two vertically mounted diffraction gratings, an upper diffraction grating forms a spectrum on an upper line of photodetectors and a lower diffraction grating forms a spectrum on a lower line of photodetectors. Such detection systems are described in WO 2011/098726.

A suitable array of photodetectors may comprise, for example, a single CCD or other type of multi-dimensional pixel detector. Preferably, the array of photodetectors comprises a single multi-linear CCD for detecting the diffracted spectra from the gratings on different lines of pixel detectors (pixels) of the CCD. An example of such a detector may comprise, for example, a single tri-linear CCD to detect the diffracted spectra from two gratings on the top and bottom lines of pixels, with the middle line of pixels providing a suitable separation distance to avoid the spectrum from one grating falling on the line of pixels designed for detecting the spectrum from the other grating.

It will be appreciated that one, two, or more so-called fixed detection channels may be provided for detecting specific spectral lines, in addition to the array detector, which detects a spectrum. Such fixed detection channels are preferably each provided by its own dedicated detector such as a photomultiplier tube (PMT) and positioned to detect a specific line characteristic of a particular element of interest.

A toroidal mirror is an aspherical mirror wherein each curvature of the two orthogonal axes (horizontal and vertical) are different, which is used to particular advantage in the present invention. The toroidal mirror preferably directs the light toward the entrance slit to provide an elongated or blurred focus, e.g. resembling a generally elliptical shape. This differs from the prior art which produces a spot or circular focus. The toroidal mirror has two focal lengths; therefore the image on the slit is a blurred or scrambled image of the object. The toroidal mirror, being aspherical, has been found to be more efficient for illuminating two or more diffraction gratings simultaneously through a single slit, i.e. with less light wastage. Preferably, the toroidal mirror makes a uniform illumination of the plurality of gratings. The generally elliptical shape of the light image produced by the toroidal mirror is better matched, for example, to the geometrical arrangement of two mounted diffraction gratings, especially two vertically mounted gratings. The elliptical shape of the light image is preferably elongated (i.e. has its long axis) vertically, i.e. in the direction of vertical mounting of the gratings. The light image at the entrance slit and/or gratings thus also preferably has a generally elliptical shape as described above.

In certain embodiments, the toroidal mirror has a horizontal radius of curvature, $R_h$, in a horizontal optical plane defined by the centre of a source of the light, the centre of the toroidal mirror and the centre of the entrance slit, which curvature defines a focal length of the mirror in the horizontal plane, and has a vertical radius of curvature, $R_v$, in a vertical plane perpendicular to the horizontal plane, which curvature defines a focal length of the mirror in the vertical plane. Preferably, $R_h$ and $R_v$ are such that the focal length in the vertical plane is shorter than the focal length in the horizontal plane. Preferably, the focal length of the mirror in the horizontal optical plane is substantially equal to, or preferably shorter than, the distance from the light source to the mirror's centre. The image of light reflected by the mirror will thus have an elliptical shape. In the case of vertically mounted gratings, the length of the elliptical image of light at the gratings is preferably oriented along the vertical direction so as to illuminate both gratings sufficiently. The width of the elliptical image at the gratings in such a case is preferably oriented in the horizontal plane so as to illuminate both gratings sufficiently once again.

The mirror is preferably mounted such that it may be tilted in one or both, preferably both, of the horizontal and vertical directions to adjust its degree of alignment. It is preferred that the centre of the mirror is substantially coincident with the optical axis of the spectrometer.

Advantageously, the toroidal mirror has been found to enable light from different regions in a source of the light to be spatially separated in the light illuminating the gratings. For example, a first diffraction grating may be preferentially illuminated with light from a first region of the light source compared to a second grating and the second grating may be preferentially illuminated with light from a second region of the light source compared to the first grating. This is especially useful where the spectrometer is a spark optical emission spectrometer wherein light is emitted from a spark source. The toroidal mirror directs light from different regions or points of the spark source such that it is spatially separated to a degree at the gratings. This has been found to reduce some spectral interference in the diffracted light since there is not such a complete mixture of spectral information in the light illuminating each grating. Instead each grating can receive light which is preferentially from a different region of the light source. Thus, if excitation events which lead to the emission of interfering spectral lines occur in different regions of the light source, then the present invention may be able to reduce the degree of spectral interference in the detected diffracted light. Preferably, one or more spectral interferences are reduced in this way. A spectral interference is interference between two or more spectral lines from different elements, i.e. where the two or more spectral lines at least partially overlap.

The toroidal mirror preferably is positioned to deflect the light through approximately 90 degrees towards the entrance slit, e.g. deflect the light emitted from a sample by approximately 90 degrees towards the entrance slit.

A beam stop optionally may be used at a point in the light's path (e.g. close before or preferably close after the entrance slit) to reduce the solid angle of the light transmitted to the gratings.

The light to be analysed emanates from a light source, which may comprise a sample to be analysed, e.g. a sample subject to excitation to cause it to emit light in the case of optical emission spectroscopy. Thus, the spectrometer further comprises a light source for producing light to be analysed. The light to be analysed, in general, may be any light from an analytical sample which carries information about the composition of the sample. The light may be transmitted, reflected or emitted by the sample.

Preferably, the light to be analysed is emission from a sample, which has been subject to, for example, a flame, plasma, arc, or spark to cause atoms of elements present in the sample to be excited and emit light of characteristic wavelengths. Most preferably, the light is arc or spark induced emission. The sample is then typically a metallic sample. In such embodiments with arc or spark induced emission, the light source therefore comprises a spark plasma from which the light to be analysed is emitted from excited elements. Such spark plasma is typically confined in a small volume not greater than about 3 mm$^3$. In such embodiments, the spectrometer preferably comprises a spark source to cause the arc or spark induced optical emission of light from a sample to be analysed, i.e. a plasma is produced by the spark source which contains the excited elements and the plasma emits light to be analysed. The spark source may be located at a distance from the mirror that is substantially the same as the focal length of the mirror. The spark source may be in a fixed position relative to the mirror. In other embodiments, for example in mobile spectrometers, the spark source may be mobile, e.g. handheld. Such handheld spark sources, often termed sparking pistols, are known that for operation are pressed against a sample to be analysed. The light from the spark plasma in the sparking pistol can be transported into the spectrometer from the plasma via one or more flexible optical fibres. The end of the one or more optical fibres from which the light emerges preferably terminates substantially where the spark plasma would be located if it were in a fixed position, e.g. at a distance from the mirror that is substantially the same as the focal length of the mirror. In that way, the optical fibre is simply situated in the spectrometer as the light source to be imaged in place of the plasma itself.

One or more optical masking systems, for example physical beam stops, which act to block light, may be used in the light path when required, e.g. to reduce even further the occurrence of spectral interference, or reduce spectral background. The masking systems act by reducing the amount of light emanating from one or more particular regions of the light source, e.g. one or more regions of a spark plasma. This enhances further the effect of reduced spectral interference provided by the degree of spatial separation of light from different regions of the light source arising from the use of the toroidal mirror. One or more masking systems may be used. The one or more masking systems may be placed either before or after (or both) the toroidal mirror. The optical masking systems may be static in the light path, or moveable in and out of the light path, as required.

The spectrometer of the present invention is particularly suitable for OES, especially spark OES, but may be useful in other types of spectroscopy where an optical configuration is required to have a plurality of diffraction gratings illuminated through the same, single entrance slit. Examples may include inductively coupled plasma optical emission spectroscopy (ICP-OES) usually for liquid samples analysis, Direct Current Arc optical emission spectroscopy (DC-Arc OES) for any kind of solid or powder samples and Rotating Electrode DC Arc spectroscopy for liquid samples analysis.

LIST OF FIGURES

FIG. 3 shows schematically in more detail the configuration of the entrance optics of an embodiment of spectrometer according to the present invention.

FIG. 4 shows an illumination pattern at the slit position in an embodiment of spectrometer according to the present invention.

FIG. 5 shows an illumination pattern at a field stop position in an embodiment of spectrometer according to the present invention.

FIG. 6 shows an illumination pattern at the two gratings in an embodiment of spectrometer according to the present invention.

DETAILED EMBODIMENTS OF THE INVENTION

The invention will now be described in more detail by way of non-limiting examples and with reference to the accompanying drawings.

Figure 1:
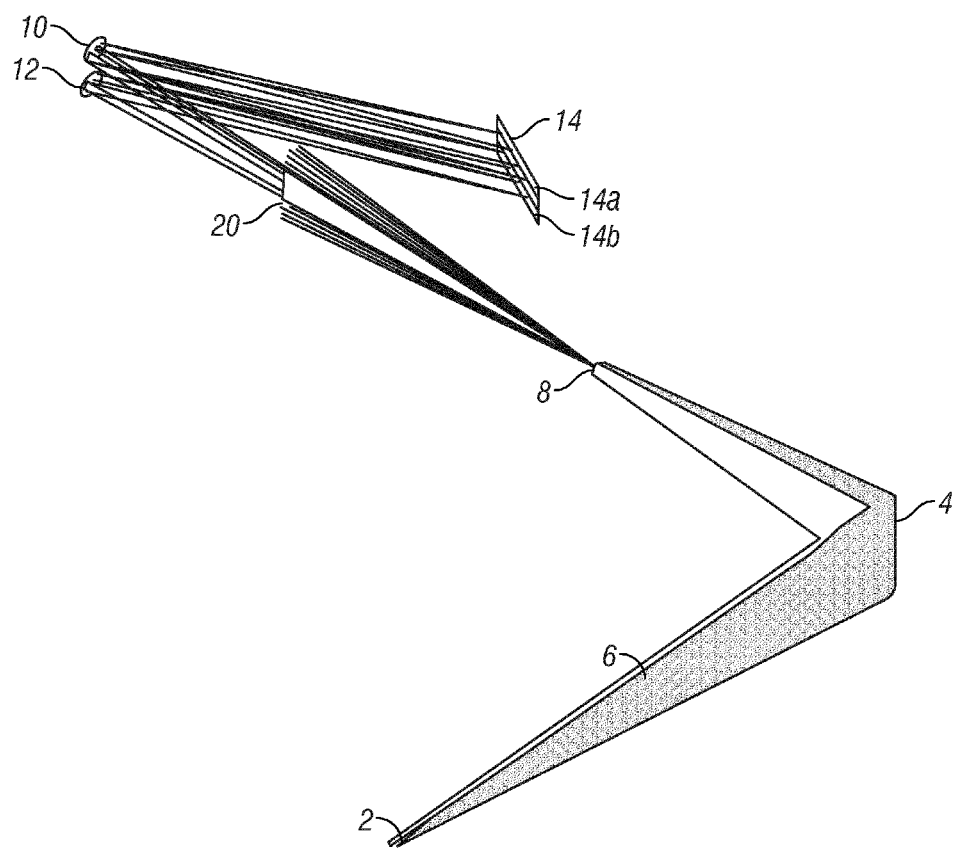
FIG. 1 shows schematically an optical layout of part of a flat field spark optical emission spectrometer embodying the present invention.

In FIG. 1 is shown a schematic optical layout of part of a flat field spark optical emission spectrometer embodying the present invention. A spark source is located at position 2 and provides light for analysis in a known manner. In the spark source an electrical spark is produced between an electrode and the surface of a solid sample that is mounted opposite the electrode. The spark rapidly vaporises a portion of the surface of the sample and produces a plasma of excited elements. The plasma emits light 6 of wavelengths that are characteristic of the elements.

The emitted light 6 from the spark source is reflected through an angle of 90 degrees by entrance optics comprising a toroidal mirror located at position 4 and thereby directed through a single primary entrance slit located at position 8. In using only a single entrance slit, only a single viewing angle of the light source and sample is required, thereby facilitating a compact design. The toroidal mirror is described in more detail below with reference to FIG. 2. An advantage of using a mirror is that the focal length is constant, in comparison to known optical systems that use focusing lenses, which always exhibit chromatic behaviour due to the dependence of the refraction index on wavelength and thus have a focal length that is wavelength dependent. A toric mirror is used so that spherical aberrations are avoided compared to spherical mirrors. In this embodiment, the use of a mirror results in a substantial bend in the light from the source to the gratings, rather than having the source and gratings substantially in-line. In this embodiment the bend is approximately 90 degrees although in other embodiments it need not be 90 degrees. The use of a mirror, required to create the elliptical illumination pattern, thus removes a direct line of sight between the source and gratings.

The light is transmitted through the entrance slit at position 8 and a reduction of the solid angle of the light may be provided by an optional field stop located at position 20. The light thereafter illuminates two holographic-made diffraction gratings 10 and 12 mounted vertically adjacent each other in a flat field mounting. The gratings, the entrance slit and the detector thus form a flat field mounted assembly. The gratings are aberration corrected flat field and imaging gratings, which are designed for high efficiency in the first order of diffraction. The gratings diffract the light and thereby disperse the light into spectral lines. The light is diffracted towards a single array detector 14, which is a tri-linear CCD in this embodiment. The two extreme lines of the CCD are used for detection. The gratings 10 and 12 each diffract the light onto different detection lines of photodetectors (pixels) of the detector. The upper grating 10 diffracts a portion of the light so that an image of a spectrum in the range 147-238 nm is formed on the first line (upper line) 14a of the tri-linear CCD. The lower grating 12 diffracts a portion of the light so that an image of a spectrum in the range 230-418 nm is formed on the third line (lower line) 14b of the tri-linear CCD. The second (middle) line of the CCD is not used for detection in this embodiment but instead provides spacing between the detection lines to avoid interference between the spectra. The spectrometer design is further kept compact in addition to using a single entrance slit by using two vertically mounted diffraction gratings and a single CCD to detect the spectra from each grating on a separate line of the detector. The arrangement of the gratings and detector after the entrance slit has been described in WO 2011/098726. Any of the grating and detection arrangements disclosed in WO 2011/098726 may be used in the present invention. The contents of WO 2011/098726 are incorporated herein in their entirety by reference.

In the described application to a spark optical emission spectrometer, the spark source, the entrance optics (mirror and slit) and the spectrograph components (gratings and detector) are purged with argon in order to produce an argon plasma and to ensure the light path has UV light transparency. The spark source comprises a sample stand, also known as a Petrey table, which is preferably inclined by 12 degrees with respect to the optical axis of the system to allow a sufficient view of the sample surface. Generally, an incline between 1.5 and 20 degrees could be used. The optical axis is contained in the horizontal plane as herein described.

Figure 2:
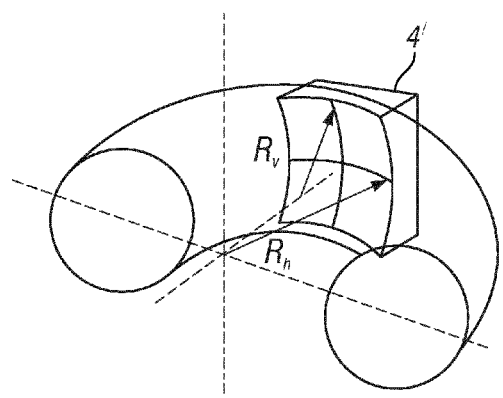
FIG. 2 shows schematically a toroidal mirror used in the present invention with its radii of curvature indicated.

With regard to the entrance optics, the two radiuses of curvature of the toroidal mirror are determined as follows. The horizontal radius of curvature, $R_h$, is chosen such that the focal length of the mirror in the horizontal optical plane defined by the centre of the spark source or plasma, the centre of the toroidal mirror and the centre of the entrance slit is voluntarily shorter than the distance from the spark plasma to the mirror's centre. This permits magnification of the source object. The vertical radius of curvature, $R_v$, is chosen such that the focal length of the mirror in the vertical plane (i.e. perpendicular to the horizontal plane) is shorter than the focal length in the horizontal plane and allows both diffraction gratings to be illuminated, i.e. to their full vertical extent. The image of light reflected by the mirror will thus have a blurred, elliptical, rather than circular, shape. The elongation of the image of light at the gratings is oriented along the vertical direction so as to illuminate both gratings sufficiently. The width of the image at the gratings is oriented in the horizontal plane so as to illuminate both gratings sufficiently. The toroidal mirror 4' is represented in FIG. 2 with the radii of curvature, $R_h$ and $R_v$, indicated and with part of the surface of the corresponding torus shown for illustration purposes. In the given embodiment, $R_h$ is 285 mm and $R_v$ is 115 mm. The focal lengths, b and c, in the horizontal and vertical planes respectively are 169 mm and 120.5 mm. The distance from the spark source to the centre of the mirror, a, is 250 mm.

The spectrometer entrance optics with dimensions a, b and c indicated are further shown schematically in FIG. 3. The left hand part of FIG. 3 shows the focusing by the toroidal mirror 4' in the horizontal plane with focal length b and the right hand part of the figure shows the focusing by the toroidal mirror in the vertical plane with shorter focal length c. The spark source is shown at position 2 together with the focal points in the horizontal ($f_h$) and vertical ($f_v$) directions. The position of the entrance slit is shown by the line s. The slit is positioned after (downstream of) the vertical focus, $f_v$, and before the horizontal focus, $f_h$, so that the illumination pattern at the slit position is somewhat blurred as shown in the zoomed image in FIG. 4 wherein the slit is shown by the vertical line 40. The illumination pattern at the field stop position 20 is elongated as shown by the elongated blurred area 42 in FIG. 5. In FIG. 5, the circular shapes represent the field stop apertures through which portions of the light will pass to illuminate the two generally circular shaped gratings 10 and 12. FIG. 6 shows the illumination pattern on the two gratings 10 and 12. By providing an illumination pattern elongated in the vertical direction the invention ensures that the gratings, which are vertically mounted, are more efficiently illuminated, i.e. with less light wastage, than with a spherical illumination pattern.

The design of the present invention advantageously allows preferentially illuminating the upper grating with light emitted by the upper part of the spark plasma, i.e. the region towards the sample surface, while preferentially illuminating the lower grating with light emitted by the lower part of the plasma, i.e. the region towards the electrode. This feature, combined with the wavelength ranges involved, allows detecting the best lines for spark optical emission spectroscopy. In spark OES, higher energy (shorter wavelength) light, including vacuum UV spectral lines, is preferentially emitted nearer the sample surface and lower energy (longer wavelength) light is preferentially emitted nearer the electrode surface.

Figure 7:
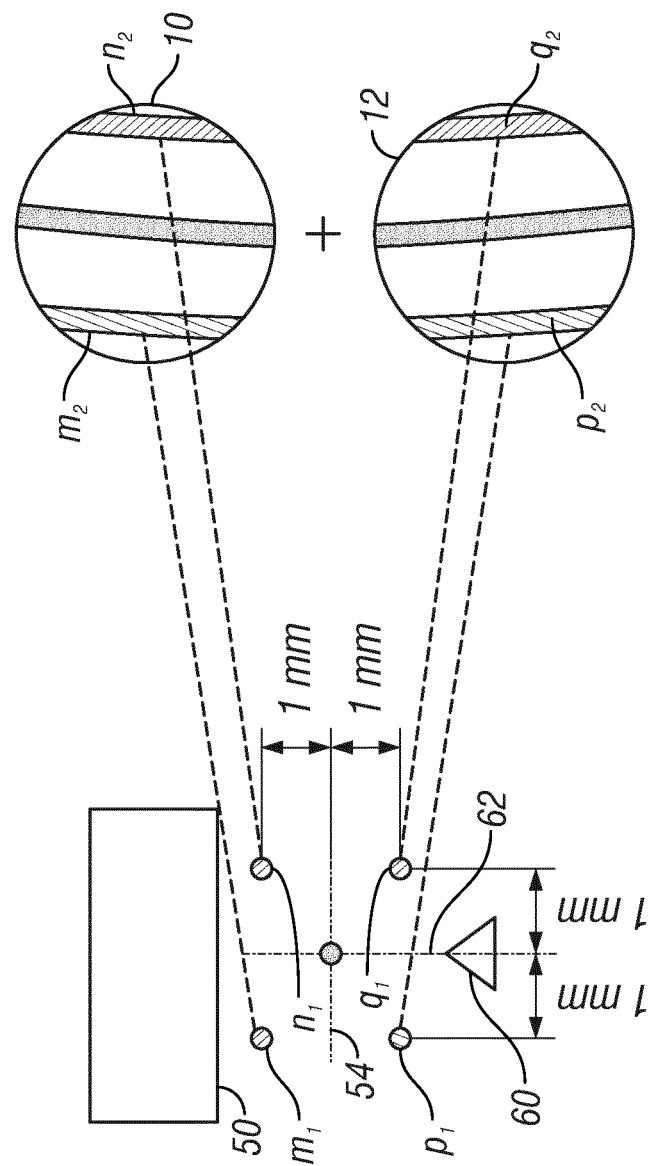
FIG. 7 shows schematically the geometrical selection of imaged areas from a spark plasma and their image construction on the two gratings in an embodiment of spectrometer according to the present invention.

This feature of geometrical selection of imaged areas from the spark plasma is illustrated in FIG. 7, which shows schematically the image construction on the two gratings 10 and 12 and the correspondence with the imaged areas from the spark plasma. On the left hand side of the figure is shown schematically the spark stand with the sample surface 50 facing the tip of the electrode 60. The electrode has a longitudinal axis 62. The optical axis of the spectrometer is denoted by line 54. Above the optical axis 54, in the upper part of the plasma, closest to the sample surface, are shown two imaged points, $m_1$ and $n_1$. The points $m_1$ and $n_1$ are 1 mm above the optical axis and lie 1 mm either side of the electrode's longitudinal axis. By means of the toroidal mirror the points $m_1$ and $n_1$ in the plasma become imaged preferentially at the upper grating 10 as depicted in the right hand side of FIG. 7. The illumination patterns on the upper grating of the points $m_1$ and $n_1$ from the plasma are the vertically elongated lines $m_2$ and $n_2$ respectively. The dotted lines in the figure are for illustration to show the correspondence between the points $m_1$ and $n_1$ and their line patterns $m_2$ and $n_2$ at the upper grating. In a similar manner, below the optical axis 54, in the lower part of the plasma, closest to the electrode, are shown two imaged points, $p_1$ and $q_1$. The points $p_1$ and $q_1$ are 1 mm below the optical axis and lie 1 mm either side of the electrode's longitudinal axis. By means of the toroidal mirror the points $p_1$ and $q_1$ in the plasma become imaged preferentially at the lower grating 12 as depicted in the right hand side of the figure. The illumination patterns on the lower grating of the points $p_1$ and $q_1$ from the plasma are the vertically elongated lines $p_2$ and $q_2$ respectively. The dotted lines show the correspondence between the points $p_1$ and $q_1$ and their line patterns $p_2$ and $q_2$ at the lower grating.

This geometrical selection of imaged points in the plasma to illuminate preferentially one or other grating may allow a reduction of certain spectral interferences. Near the sample surface the discharge plasma is hotter than elsewhere in the spark stand and allows ionization of elements and excitation of ionic-type emission lines, which require high excitation energy. In contrast, atomic-type transition lines, with relatively lower excitation energies compared to ionic-type emission lines, are emitted preferentially in the relatively cooler centre of the discharge gap between the sample and electrode, situated near the optical axis of the spectrometer.

Figure 8A:
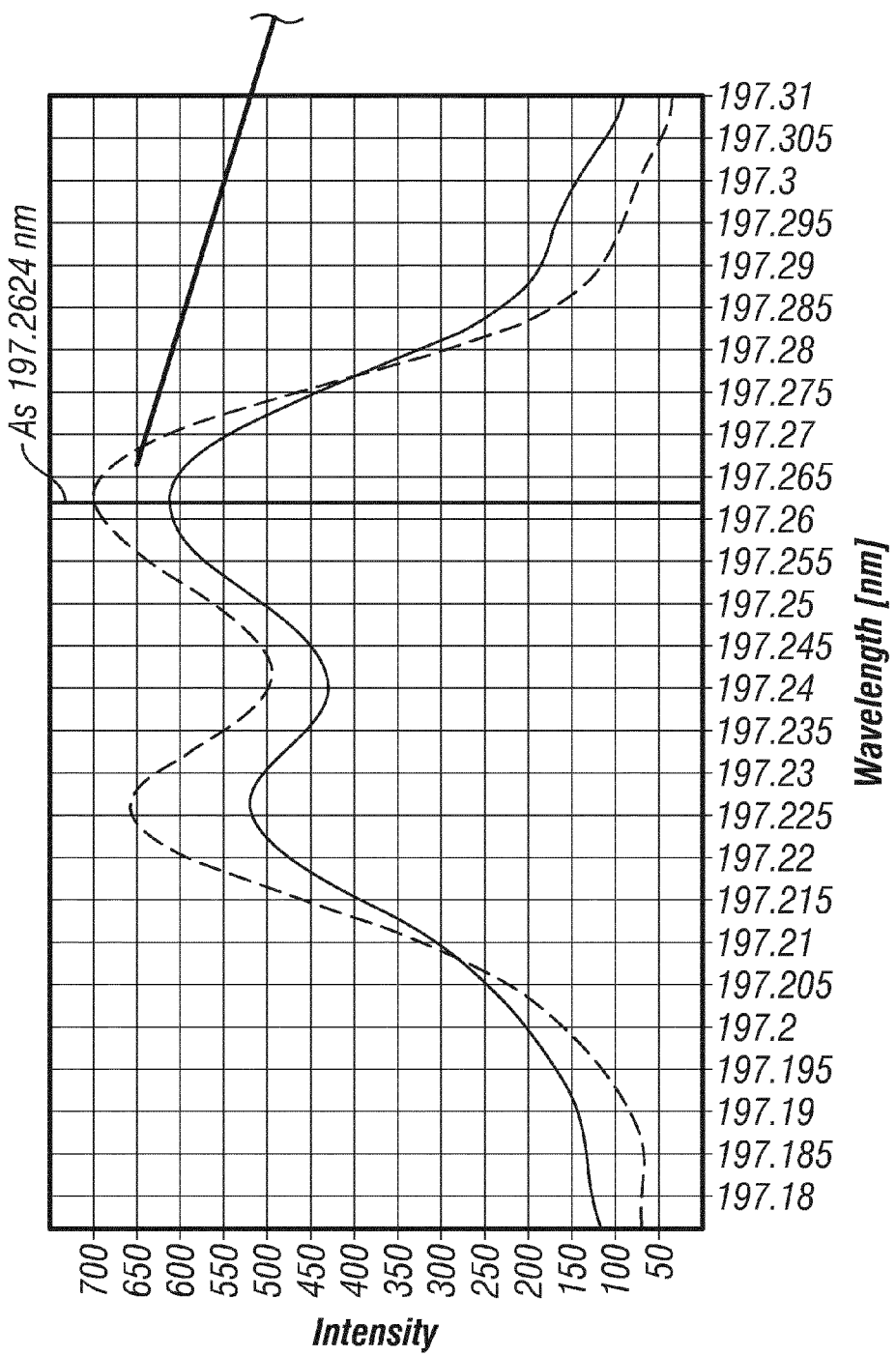
FIGS. 8A and 8B show spectra of an arsenic spectral line obtained without masking and with masking respectively in an embodiment of spark optical emission spectrometer according to the present invention
Figure 8B:
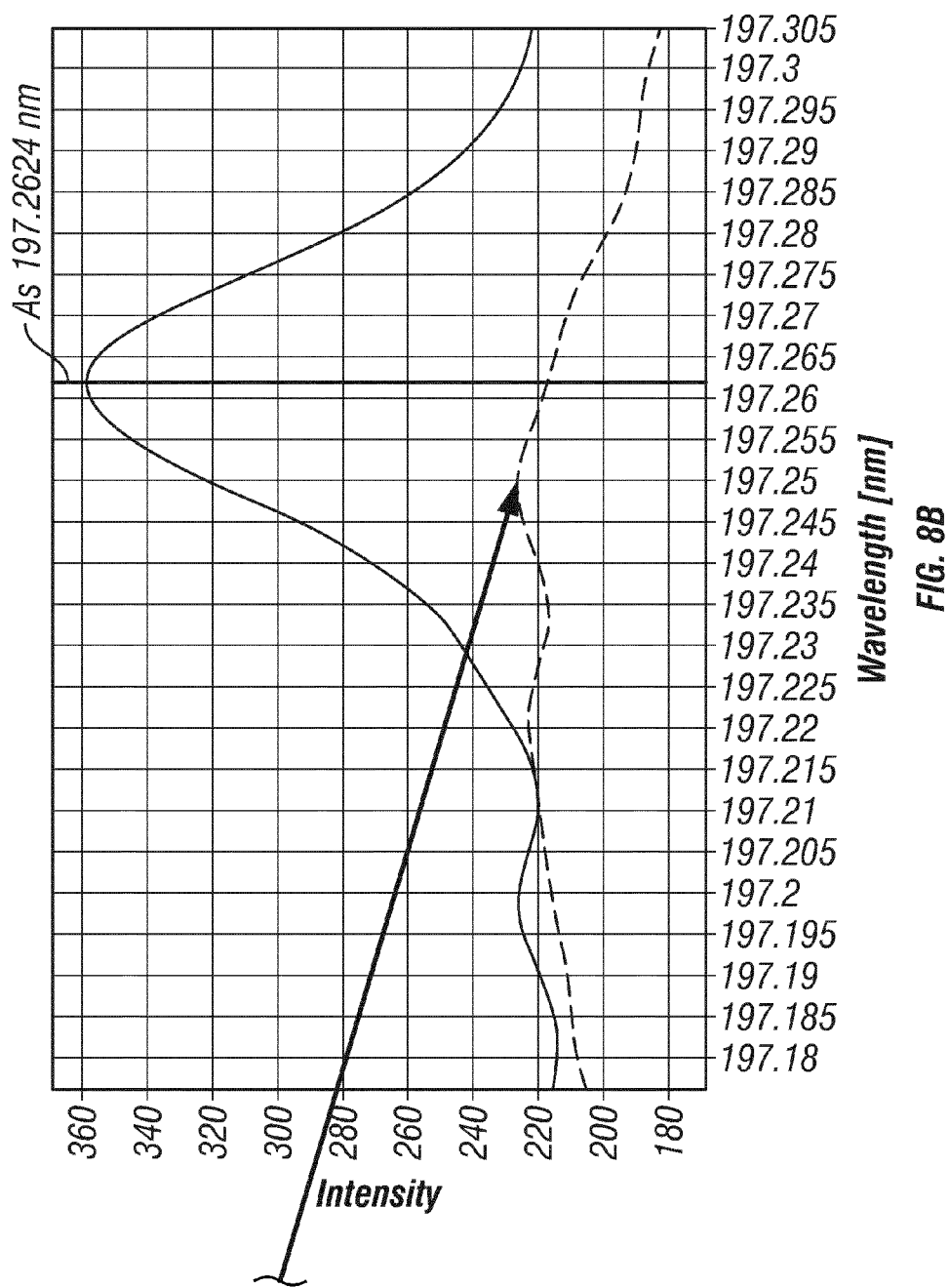

In certain embodiments, the efficiency of separating interfering lines can be enhanced further by the use of optical masks. In one embodiment, the spectral lines directed to, for example, the upper grating from near the sample surface can optionally be masked with a mechanical mask placed in the path of the light from near the sample surface to the mirror allowing reduction of the ionic emission-type spectral lines and thus reducing the spectral complexity and potential interferences in the emission spectrum. In FIGS. 8A (spectrum obtained without masking) and 8B (spectrum obtained with masking) is shown such an example of the effect of masking the sample surface. The FIGS. 8A and 8B show part of a spark emission spectrum from an RN19 steel reference sample (containing 600 ppm As), which is shown by the solid curve, and the corresponding part of a spark emission spectrum from a pure iron sample, which is shown by the dotted curve. In this particular case, as shown in FIG. 8A, the arsenic (As) 197.2624 nm line, from the RN19 reference sample, is interfered with by the iron (Fe) 197.224 nm line. The As 197.2624 is an atomic-type transition line, with excitation energy of 6.28 eV and is emitted preferentially in the centre of the discharge gap, situated near the optical axis, while the Fe 197.224 nm line is an ionic type transition line, with excitation energy of 17.86 eV, which is emitted near the sample's surface. By masking of the sample surface the Fe line contribution is drastically reduced and the As line can be detected with greater sensitivity as shown in FIG. 8B.

As mentioned above, an advantage of the toroidal mirror is to create an illumination pattern that is elliptical in order to illuminate both gratings at the same time with high efficiency. In contrast, with a spherical mirror or a lens, the highest light intensity is in the axis passing through the centre of the mirror or of the lens. The size of the spot in the case of the lens will depend on the wavelength, due to the dependence of the refractive index on the wavelength.

As a variation of the spectrometer design described above, instead of having the spark plasma fixed in position substantially at the focal length from the mirror, the spark plasma can be replaced at that position by the ends of one or more optical fibres, where the one or more optical fibres are for collecting and transmitting light to the spectrometer from a spark plasma that is situated remotely from the spectrometer. Such fibre optics arrangements are typically used for mobile spark OES instruments where they are used to transport the light from a mobile spark stand, such as, for example, the known handheld spark stands that are pistol shaped and operated by pressing the sparking pistol against the material to be analyzed.

In view of the above description it can be seen that the present invention provides an improved spectrometer and method of spectroscopy.

Unless the context clearly indicates otherwise, as used herein plural forms of the terms herein are to be construed as including the singular form and vice versa.

Any steps in a process described herein may be performed in any order, unless stated otherwise or unless the context clearly requires otherwise.

Throughout the description and claims of this specification, the words "comprise", "including", "having", "contain" and the like and variations of the words, for example "comprising" and "comprises" etc, mean "including but not limited to", and are not intended to (and do not) exclude other components.

The use of examples, or exemplary language (including "for instance", "such as", "for example" and similar phrases) herein, is intended merely to better illustrate the invention and does not indicate a limitation on the scope of the invention unless otherwise claimed. No language in the specification should be construed as indicating any non-claimed element as essential to the practice of the invention.

It will be appreciated that variations to the foregoing embodiments of the invention can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features.

All of the features disclosed in this specification may be combined in any combination, except combinations where at least some of such features and/or steps are mutually exclusive. In particular, the preferred features of the invention are applicable to all aspects of the invention and may be used in any combination. Likewise, features described in non-essential combinations may be used separately (not in combination).

It will be appreciated that many of the features described above, particularly of the preferred embodiments, are inventive in their own right and not just as part of an embodiment of the present invention. Independent protection may be sought for these features in addition to or alternative to any invention presently claimed.

The invention claimed is:

1. A spark optical emission spectrometer comprising:
   a spark source comprising an electrode configured to produce a spark induced emission of light from a sample;
   a single entrance slit;
   a toroidal minor comprising a first radius of curvature in a horizontal plane and a second radius of curvature in a vertical plane and configured to direct the light through the single entrance slit, wherein the first radius of curvature and the second radius of curvature are different;

a plurality of diffraction gratings configured to simultaneously diffract light directed through the entrance slit by the toroidal mirror; and a detector configured to detect the diffracted light from the plurality of diffraction gratings, wherein the toroidal minor directs the light through the entrance slit such that the light emitted from different regions in the spark source is spatially separated whereby a first diffraction grating is illuminated with light emitted from a first region of the spark source compared to a second diffraction grating illuminated with light emitted from a second region of the spark source.

2. A spectrometer as claimed in claim 1 wherein the toroidal minor is placed before the entrance slit for collecting light directly from the spark source without any intervening optics.

3. A spectrometer as claimed in claim 1 wherein the toroidal minor forms an elliptical image of the light.

4. A spectrometer as claimed in claim 1 wherein one or more spectral interferences are resolved in the diffracted light detected at the detector.

5. A spectrometer as claimed in claim 1 wherein the spectrometer further comprises one or more optical masking systems configured to reduce the amount of light emitted from one or more particular regions of the spark source.

6. A spectrometer as claimed in claim 1 wherein the toroidal minor is positioned to deflect the light from the spark source through approximately 90 degrees towards the entrance slit.

7. A spectrometer as claimed in claim 1 wherein the first and second diffraction gratings are mounted vertically with respect to each other.

8. A spectrometer as claimed in claim 1 wherein the first and second gratings are mounted at substantially the same distance as each other from the entrance slit and substantially the same distance as each other from the detector.

9. A spectrometer as claimed in claim 1 wherein each grating forms a spectrum on the detector in a different spectral range to the other grating(s) and the spectra together cover at least the spectral range from 147 to 418 nm.

10. A spectrometer as claimed in claim 1 wherein the detector comprises an array of photodetectors that includes a plurality of separate lines of photodetectors and each grating forms a spectrum on a separate line of photodetectors.

11. A spectrometer as claimed in claim 1 wherein the first region comprises a region near a surface of the sample.

12. A spectrometer as claimed in claim 1 wherein the second region comprises a region near a surface of the electrode.

13. A spectrometer as claimed in claim 1 wherein the light emitted from the first region comprises a high energy.

14. A spectrometer as claimed in claim 13 wherein the high energy produces ionic-type emission lines.

15. A spectrometer as claimed in claim 1 wherein the light emitted from the second region comprises a low energy.

16. A spectrometer as claimed in claim 1 wherein the low energy produces atomic-type emission lines.

17. A spectrometer as claimed in claim 1 wherein the light detected from the first diffraction grating comprises a reduced degree of spectral interference with the light detected from the second diffraction grating.

18. A method of spark optical emission spectroscopy comprising:

directing spark induced emission of light from a spark source comprising an electrode through an entrance slit using a toroidal mirror comprising a first radius of curvature in a horizontal plane and a second radius of curvature in a vertical plane;

simultaneously illuminating a plurality of diffraction gratings with the light directed through the entrance slit, whereby each diffraction grating diffracts a portion of the light; and detecting the diffracted light from the plurality of diffraction gratings using at least one array detector;

wherein the toroidal mirror directs the light through the entrance slit such that light emitted from different regions in the spark source is spatially separated whereby a first diffraction grating is illuminated with light emitted from a first region of the spark source and simultaneously a second diffraction grating is illuminated with light emitted from a second region of the spark source.

* * * * *